(12) United States Patent
Ning et al.

(10) Patent No.: US 9,392,986 B2
(45) Date of Patent: Jul. 19, 2016

(54) METHOD AND APPARATUS FOR CONE BEAM BREAST CT IMAGE-BASED COMPUTER-AIDED DETECTION AND DIAGNOSIS

(75) Inventors: Ruola Ning, Fairport, NY (US); Xiaohua Zhang, Rochester, NY (US); David L. Conover, Rochester, NY (US); Shaohua Liu, Rochester, NY (US)

(73) Assignees: University of Rochester, Rochester, NY (US); Koning Corporation, West Henrietta, NY (US)

(*) Notice: Subject to any disclaimer, the term of this patent is extended or adjusted under 35 U.S.C. 154(b) by 195 days.

(21) Appl. No.: 13/985,517

(22) PCT Filed: Feb. 14, 2012

(86) PCT No.: PCT/US2012/025141
§ 371 (c)(1),
(2), (4) Date: Oct. 22, 2013

(87) PCT Pub. No.: WO2012/112627
PCT Pub. Date: Aug. 23, 2012

(65) Prior Publication Data
US 2014/0037044 A1  Feb. 6, 2014

Related U.S. Application Data

(60) Provisional application No. 61/442,559, filed on Feb. 14, 2011.

(51) Int. Cl.
G06T 7/00 (2006.01)
A61B 6/00 (2006.01)
A61B 6/03 (2006.01)
G06F 19/00 (2011.01)

(52) U.S. Cl.
CPC ............ *A61B 6/502* (2013.01); *A61B 6/032* (2013.01); *A61B 6/5217* (2013.01); *G06T 7/0012* (2013.01); *G06F 19/321* (2013.01); *G06T 2207/10081* (2013.01); *G06T 2207/30068* (2013.01)

(58) Field of Classification Search
None
See application file for complete search history.

(56) References Cited

U.S. PATENT DOCUMENTS 7,362,845 B2   4/2008  Ning
7,693,318 B1   4/2010  Stalling et al.
(Continued)

OTHER PUBLICATIONS

Feng et al, A software-based x-ray scatter correction method for breast tomosynthesis, Medical Physics 38 (12), Dec. 2011, pp. 6643-6653.*

*Primary Examiner* — Utpal Shah
*Assistant Examiner* — Mai Tran
(74) *Attorney, Agent, or Firm* — Cooper & Dunham, LLP

(57) ABSTRACT

Cone Beam Breast CT (CBBCT) is a three-dimensional breast imaging modality with high soft tissue contrast, high spatial resolution and no tissue overlap. CBBCT-based computer aided diagnosis (CBBCT-CAD) technology is a clinically useful tool for breast cancer detection and diagnosis that will help radiologists to make more efficient and accurate decisions. The CBBCT-CAD is able to: 1) use 3D algorithms for image artifact correction, mass and calcification detection and characterization, duct imaging and segmentation, vessel imaging and segmentation, and breast density measurement, 2) present composite information of the breast including mass and calcifications, duct structure, vascular structure and breast density to the radiologists to aid them in determining the probability of malignancy of a breast lesion.

22 Claims, 4 Drawing Sheets

(56) References Cited

U.S. PATENT DOCUMENTS

| | | |
|---|---|---|
| 7,697,660 B2 | 4/2010 | Ning |
| 2007/0211930 A1 | 9/2007 | Dolwick et al. |
| 2009/0171244 A1* | 7/2009 | Ning ................ A61B 6/032 600/567 |
| 2009/0274354 A1* | 11/2009 | Ng ................ A61B 6/025 382/131 |
| 2010/0119139 A1* | 5/2010 | Bertram ............ G06T 11/005 382/131 |
| 2011/0150313 A1* | 6/2011 | Su ................ G06T 7/2026 382/132 |

* cited by examiner

METHOD AND APPARATUS FOR CONE BEAM BREAST CT IMAGE-BASED COMPUTER-AIDED DETECTION AND DIAGNOSIS

REFERENCE TO RELATED APPLICATION

The present application is a national stage of PCT/US2012/025141, filed Feb. 14, 2012, which claims the benefit of U.S. Provisional Patent Application No. 61/442,559, filed Feb. 14, 2011, the entire disclosures of which are hereby incorporated by reference in their entirety into the present disclosure.

STATEMENT OF GOVERNMENT INTEREST

This invention was made with government support under Grant Nos. R01 9 HL078181 and 4 R33 CA94300 awarded by National Institutes of Health. The government has certain rights in the invention.

FIELD OF THE INVENTION

The present invention is directed to breast imaging and more particularly to the provision of three-dimensional (3D) breast information, including 3D location and measurement of mass and calcifications, 3D duct structure, 3D vascular structure, and volumetric breast density.

DESCRIPTION OF RELATED ART

Many researchers have made significant progress in breast lesion auto detection on mammograms and Breast MRI (BMRI). Computer-aided auto-detection technology in those two imaging modalities has achieved good results. However, mammography and MRI have their inherent limitations. Due to breast tissue overlap, even large tumors and some calcification clusters are obscured in mammograms.

Although it is reported that CAD (computer-aided detection and diagnosis) on mammography increases sensitivity, it is also reported that there is no significant improvement with the CAD applied to the mammograms. The effectiveness of the CAD application to mammography seems unclear.

BMRI cannot detect calcifications, which are important signs for early breast cancer and DCIS, and are evident in up to 50% of breast cancers not associated with a mass. Although it is a three-dimensional (3D) visualization of the breast, BMRI has limited spatial resolution (in-plane resolution of ~1 mm and slice thickness of 2-3 mm). Small lesions may be missed or incorrectly characterized due to the resolution limitation.

Although BMRI-based CAD has had some success in distinguishing benign from malignant masses, acknowledged limitations of the system include an inability to consider T2-weighted images. Thus, the system potentially may miss useful additional morphology information available in those sequences. In addition, current BMRI-based CAD cannot improve radiologist accuracy in distinguishing malignant from benign MRI screen-detected lesions because of its poor DCIS detection sensitivity.

Another breast imaging modality is digital breast tomosynthesis (DBT), which has a sensitivity of up to 85%. However, DBT collects projections over limited angles, resulting in spatial resolution loss in the direction perpendicular to the detector. Although CAD in DBT can help radiologists to handle a large amount of data, the resolution loss limits its ability to detect subtle breast lesions and calcification clusters, so that it is likely that DBT must be used with digital mammography for breast cancer screening and diagnosis.

Ultrasound-based CAD (US-CAD) has also been explored. Though ultrasound has considerable potential, it also has well known limitations. The technique is difficult to teach and perform. Also, differentiating between benign and malignant lesions can be challenging. The addition of ultrasound could also lead to unnecessary biopsies of benign lesions. Another major limitation of US-CAD is the fact that microcalcifications are difficult to image with ultrasound. In addition, US-CAD is limited by the relatively poor spatial resolution of ultrasound. In summary, different breast imaging modalities have different characteristics that require the development of the modality-based CAD to further improve radiologists' accuracy and efficiency.

Radiographic breast parenchymal pattern, also referred to as breast density, is an important factor associated with the development of breast cancer. Currently, most breast density research is based on mammography technology. Most breast density description uses the BI-RADS breast density terminology. In BI-RADS, four categories of breast density are defined:

Type 1. Almost entirely fat: glandular tissue <25%;
Type 2. Scattered fibroglandular tissues: glandular tissue 25%-50%;
Type 3. Heterogeneously dense: glandular tissue 51%-75%; and
Type 4. Extremely dense: glandular tissue >75%.

However, breast tissue overlaps in two-dimensional mammography projection images. The breast density measurement may be inaccurate using mammograms.

In summary, different breast imaging modalities have different characteristics that require the development of the modality-based CAD to further improve radiologists' accuracy and efficiency.

SUMMARY OF THE INVENTION

There is thus a need in the art for a CAD system working with CBBCT images to provide 3D composite breast information.

There is also a need in the art to improve accuracy and efficiency in radiologists' diagnostic performance.

It is therefore an object of the invention to meet those needs.

It is therefore a primary object of the invention to provide 3D composite breast information, which includes breast density evaluation, mass and calcification detection and measurement, breast vascular structure segmentation, and breast duct segmentation.

It is another object of the invention to provide method to accurately evaluate breast density with CBBCT images.

It is yet another object of the invention to provide three-dimensional location information of breast masses with CBBCT images.

It is yet another object of the invention to provide three-dimensional characteristics of breast masses with CBBCT images.

It is yet another object of the invention to provide three-dimensional location information of breast calcifications with CBBCT images.

It is yet another object of the invention to provide three-dimensional characteristics of breast calcifications with CBBCT images.

It is yet another object of the invention to provide three-dimensional characteristics of breast vascular system with CBBCT images.

It is yet another object of the invention to provide three-dimensional characteristics of breast ducts with CBBCT images.

To achieve the above and other objects, the present invention is directed to a CAD technique based on cone-beam breast computed tomography (CBBCT). Cone Beam Breast CT is a three-dimensional breast imaging modality with soft tissue contrast superior to that of mammography, high contrast resolution and no tissue overlap. With those advantages, it is possible to measure volumetric breast density accurately and quantitatively with CBBCT 3D images. Cone Beam Breast CT is a novel breast imaging technology, using cone beam CT technology and an ergonomically designed imaging system. CBBCT delivers true three-dimensional breast images without tissue overlap. The resolution of CBBCT images is 3D isotropic, with the voxel size as small as 155 µm. Even without intravenous contrast injection, the CBBCT soft tissue contrast-to-noise ratio is as high as 8. The breast coverage of CBBCT is comparable to and even larger than that of mammography. With those novel features, CBBCT images of the breast can be an ideal tool to quantitatively measure volumetric density of the breast.

CBBCT-based computer aided diagnosis (CBBCT-CAD) technology is a clinically useful tool for breast cancer detection and diagnosis that will help radiologists to make more efficient and accurate decisions. The CBBCT-CAD is able to: 1) use 3D algorithms for image artifact correction, mass and calcification detection and characterization, duct imaging and segmentation, vessel imaging and segmentation, and breast density measurement, 2) present composite information of the breast including mass and calcifications location and characteristics, duct structure, vascular structure and breast density to the radiologists to aid them in determining the probability of malignancy of a breast lesion.

The novelties of the CBBCT-CAD system include: 1) The first 3D CAD system based on CBBCT technology; 2) The first CAD system to provide composite breast information that is not available from other modalities-based CAD systems; 3) Prominent accuracy and efficiency improvements in radiologists' diagnostic performance.

Publications related to the present invention include:

James C. Bezdek, "Pattern Recognition with Fuzzy Objective Function Algorithms", Kluwer Academic Publishers, Norwell, Mass., 1981

Xiaohua Zhang, Ruola Ning and Dong Yang, "Three dimensional breast masses auto detection in cone beam breast CT," Proc. SPIE 2009; 7260: 726027.

Xiaohua Zhang, Ruola Ning and Jiangkun Liu, "Computer aided breast calcification auto-detection in cone beam breast CT," Proc. SPIE 2010; 7624: 76242M.

D Chen, R Fahmi, A A Farag, R L Falk, G W Dryden, "Accurate and fast 3D colon segmentation in CT colonography," Proc. of ISBI 2009; 490-493.

Dong Yang, Ruola Ning, Yong Yu, David Conover and Xianghua Lu, "Implementation and evaluation of the half-scan scheme based on CBCT (cone-beam CT) system" Proc. SPIE 5368, 542 (2004).

The following related patents are hereby incorporated by reference into the present disclosure:

1. U.S. Pat. No. 8,023,767 Method and apparatus for 3D metal and high-density artifact correction for cone-beam and fan-beam CT imaging 2. U.S. Pat. No. 7,949,095 Methods and apparatus for differential phase-contrast fan beam CT, cone-beam CT and hybrid cone-beam CT 3. U.S. Pat. No. 7,697,660 Apparatus and method for cone beam computed tomography breast imaging 4. U.S. Pat. No. 7,643,605 Method and apparatus for cone beam CT dynamic imaging 5. U.S. Pat. No. 7,362,845 Method and apparatus of global de-noising for cone beam and fan beam CT imaging 6. U.S. Pat. No. 6,987,831 Apparatus and method for cone beam volume computed tomography breast imaging 7. U.S. Pat. No. 6,618,466 Apparatus and method for x-ray scatter reduction and correction for fan beam CT and cone beam volume CT 8. U.S. Pat. No. 6,504,892 System and method for cone beam volume computed tomography using circle-plus-multiple-arc orbit 9. U.S. Pat. No. 6,480,565 Apparatus and method for cone beam volume computed tomography breast imaging 10. U.S. Pat. No. 6,477,221 System and method for fast parallel cone-beam reconstruction using one or more microprocessors 11. U.S. Pat. No. 6,298,110 Cone beam volume CT angiography imaging system and method 12. U.S. Pat. No. 6,075,836 Method of and system for intravenous volume tomographic digital angiography imaging 13. U.S. Pat. No. 5,999,587 Method of and system for cone-beam tomography reconstruction

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
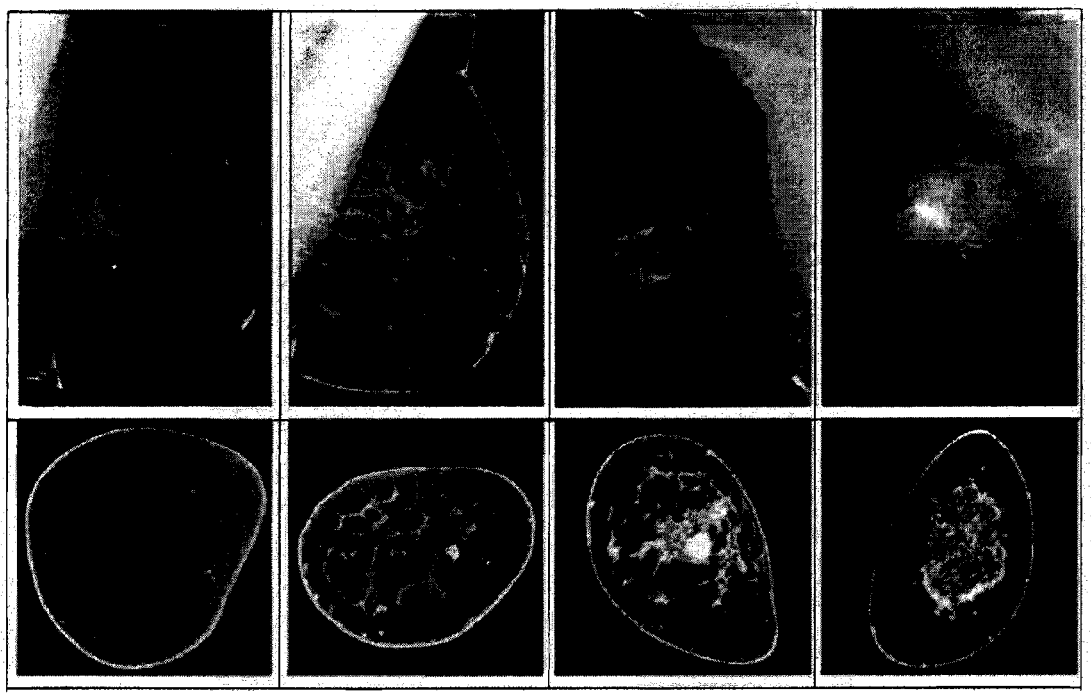
FIG. 1 is a set of images showing a comparison between mammography and CBBCT images.

A preferred embodiment will be set forth in detail with reference to the drawings, in which like reference numerals refer to like elements or steps throughout.

The first step is skin removal. Although the skin in CBBCT images has higher intensity than the fatty stroma, its intensity is only slightly higher than that of the glandular tissue. A simple thresholding cannot segment the skin from other tissue. Based on the fact that the skin is on the outermost layer of the whole breast, a morphological process is proposed to remove the skin from the breast in CBBCT images.

1. A histogram thresholding method is applied to the whole CBBCT image volume to separate the image into three distinct parts which have significant different intensities: air, fat and tissues (including skin and glands).

2. Based on the fact that the skin is between the inner breast and the air, a morphological 3D erosion operation is applied to erode the tissue between air and fat.

3. When the erosion kernel reaches the fat area in the inner breast, the erosion stops.

4. In case the glandular tissue is connected to the skin in CBBCT images, during the erosion, a global ratio of fat area vs. total edge area is recorded along the edge of the breast. When the ratio reaches 80% (or another suitably chosen value), the skin removal process stops.

Glandular tissue segmentation will now be explained. The fuzzy c-means (FCM) algorithm is widely used for image segmentation. It is also used for breast density assessment in both mammography and breast MRI. In CBBCT images, due to the high soft tissue contrast, FCM is also an effective algorithm to segment glandular tissue from fat. The FCM is taught in James C. Bezdek, "Pattern Recognition with Fuzzy Objective Function Algorithms", Kluwer Academic Publishers, Norwell, Mass., 1981.

In the fuzzy c-means clustering algorithm, an objective function is defined as:

$$J_m = \sum_{i=1}^{N} \sum_{j=1}^{C} u_{ij}^m \|x_i - c_j\|^2$$

where $x_i$ is the data vector to be clustered, $c_j$ is the center vector of the jth cluster, $u_{ij}$ is the degree of the vector $x_i$ in the jth cluster, m is the fuzziness exponent, N is the number of total data vectors, and C is the number of total clusters. $\|*\|$ is a distance function measuring the similarity between any data vector and cluster center.

The fuzzy c-means clustering algorithm iteratively optimizes the objective function $J_m$ by updating $u_{ij}$ and $c_j$ with $$c_j = \frac{\sum_{i=1}^{N} u_{ij}^m x_i}{\sum_{i=1}^{N} u_{ij}^m}, \quad u_{ij} = \frac{1}{\sum_{k=1}^{C} \left(\frac{\|x_i - c_j\|}{\|x_i - c_k\|}\right)^{\frac{2}{m-1}}}$$

The algorithm stops when $\max_{ij}\{|u_{ij}^{(k+1)} - u_{ij}^k|\} < \epsilon$, where $\epsilon$ is the termination parameter between 0 and 1. The cluster number C is set to 3. Each cluster represents air, fat, and glands.

Bias areas include low density glandular tissue with attenuation (as measured in Hounsfeld units, or HU) close to the fat and non-uniform areas caused by imaging artifacts. To achieve better accuracy of tissue segmentation, the bias areas need to be handled. In addition to the clusters for air, fat and glands, an extra cluster is used for bias areas.

To further assign voxels in a bias area into the three clusters. the following process is used:

1. A local contrast process is applied to the CBBCT images after skin removal. The local contrast is based on the following equation:

$$f(x, y, z) = f(x, y, z) - \min_{(p,q,r) \in R} f(p, q, r)$$

Here, f(x,y,z) is the HU of a voxel at a position (x,y,z), and R is a local cube with size N×N×N. By this process, the non-uniform artifact is reduced.

2. Voxels in the bias area are extracted to go through a second clustering using the images from step 1. The cluster number here is set to 3. The cluster with the highest center value is considered to be glands, and the rest of clusters are considered to be fat.

3. Combine the clustering results from first clustering and second clustering to yield a final result of air, fat and gland segmentation.

After the CBBCT images are segmented into skin, fat and glands, the percentage of each tissue with respect to the whole breast volume can be calculated.

Experimental results will now be discussed.

From the CBBCT clinical database, 5 patient data sets were selected for a preliminary experiment. Each patient data set had its mammography records reviewed by a radiologist, and its breast density category was assigned based on the mammograms. The computer aided breast density evaluation was applied to the CBBCT images of each patient. FIG. 1 shows the mammograms and the CBBCT slices of 4 cases used in this study, corresponding to the 4 BI-RADS breast density categories. More specifically, that figure shows four clinical cases with MLO mammogram images and CBBCT slice images. Top row: mammography images; Bottom row: corresponding CBBCT slices. Left column: BIRADS-1 (fatty) breast; Middle left column: BIRADS-2 (scattered) breast; Middle right column: BIRADS-3 (Hetero dense) breast; Right column: BIRADS-4 (Extreme dense) breast.

Figure 2:
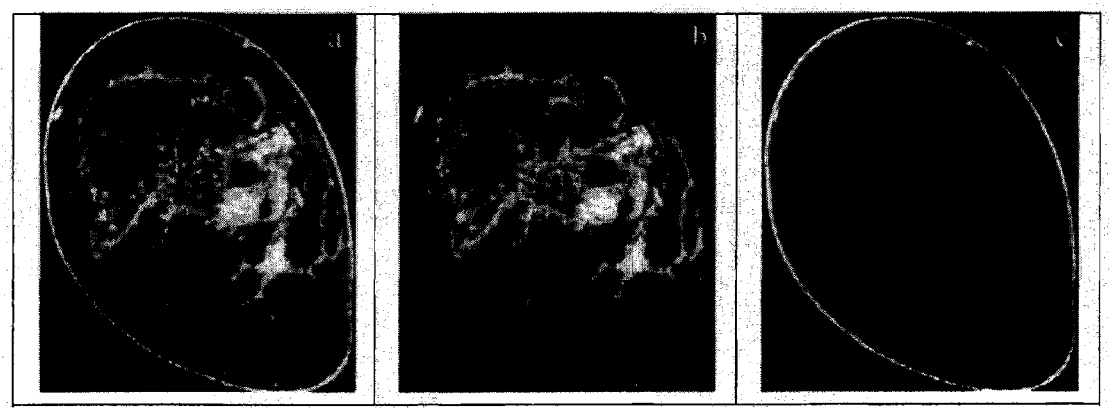
FIG. 2 is a set of images showing skin removal results.
Figure 3:
FIG. 3 is a set of images showing the auto-segmentation of an image.

The CBBCT breast density auto-evaluation process is applied to each of the clinical cases. FIG. 2 shows the skin removal results, and FIG. 3 shows the auto-segmentation results. More specifically, FIG. 2 shows a) original CBBCT image, b) CBBCT image with skin removed, and c) skin image. FIG. 3 shows a) original CBBCT image with skin removed, b) fat tissue area, and c) glandular tissue area.

Based on the segmented image, the percentages of skin, fat, and glands could be acquired. Table I lists the density measurement and compares it with the BI-RADS category of each case.

| Case Number | Mammography BI-RADS Category | CBBCT Measurement | | |
|---|---|---|---|---|
| | | Gland (%) | Fat (%) | Skin (%) |
| 1 | Fatty | 5.23 | 81.52 | 13.25 |
| 2 | Scattered | 24.91 | 63.42 | 11.67 |
| 3 | Hetero Dense | 23.79 | 63.50 | 12.71 |
| 4 | Hetero Dense | 8.97 | 79.23 | 11.79 |
| 5 | Extreme Dense | 13.21 | 65.03 | 21.75 |

Breast density changes over time. An increase in breast density is associated with greater risk of breast cancer, regardless of the original breast density measurement. Accurate measurement over time is important for active surveillance of the breast density change. The breast density auto-evaluation provides accurate volumetric measurement to detect the changes of density; hence timely cancer risk assessment can be possible.

Table I above gives the comparison result between CBBCT breast density measurement and the mammography based BI-RADS category. As can be seen from the table, there are obvious disagreements between those two systems, especially within breasts with higher density categories in BI-RADS. Measuring breast density with two-dimensional mammograms and true three-dimensional CBBCT images can yield different results for the same breast. A new breast density measurement system may be defined based on CBBCT images.

The preferred embodiment is not limited to measuring breast density. Mass detection and calcification detection will now be disclosed. The algorithm is taught in Xiaohua Zhang, Ruola Ning and Dong Yang, "Three dimensional breast masses auto detection in cone beam breast CT," Proc. SPIE 2009; 7260: 726027.

Abnormal density and structural distortion are radiographic signs for radiologists to detect masses. In 3D CBBCT images, breast masses are observed as congregated volumetric regions which have a denser structure than the surrounding normal tissues. Malignant masses have irregular or spiculated margins, while benign masses usually have smooth margins. The high contrast of CBBCT images reveals the density difference between tissues. A 3D mass detection algorithm takes advantage of high contrast resolution and the 3D characteristic of the CBBCT images.

In CBBCT, high contrast resolution reveals the contrast changes of tissue components across voxels. The 3D detection algorithm is able to measure these changes and uses the difference between masses and normal tissues for suspicious region detection. According to the preliminary study on 14 pathology-proven masses, after image calibration, the average contrast between masses and their surrounding tissues ranged from 10 to 80 HU. Other characteristics, such as the gradient congregation of the mass, were also used to distinguish mass from normal tissue. In the preliminary studies, a 3D weighted average algorithm was applied, followed by a 3D iris filtering to CBBCT volume images to highlight the congregate tissue volume. The highlighted areas are selected as candidates of breast masses. In the preliminary result, 12 of the 14 masses were correctly detected. After the mass regions are detected, the corresponding measurements of each region are calculated. The measurements include density, size, volume and shape descriptors. The marked results and corresponding measurements will be provided as output results.

Figure 4:
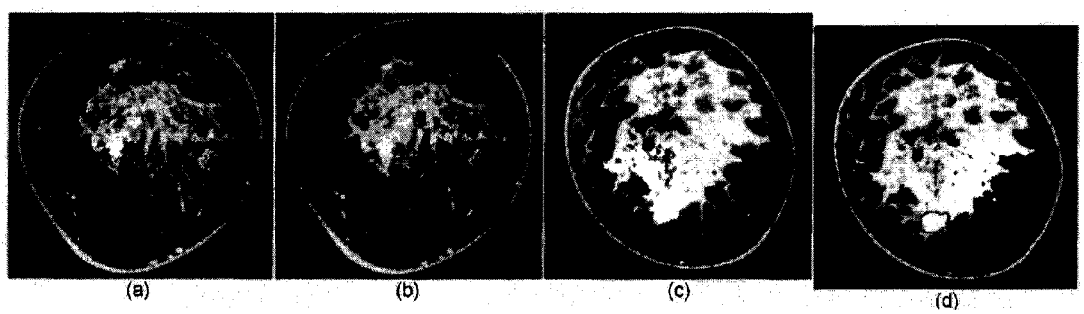
FIG. 4 is a set of images showing mass detection.

FIG. 4 shows the results of preliminary studies on mass detection. Images (a) and (c) show pathology-proven masses. Images (b) and (d) show the results of automatic mass detection.

Figure 5:
FIG. 5 is a set of images showing calcification detection.

Calcification detection will now be disclosed. The algorithm is taught in Xiaohua Zhang, Ruola Ning and Jiangkun Liu, "Computer aided breast calcification auto-detection in cone beam breast CT," Proc. SPIE 2010; 7624: 76242M. In CBBCT images, calcifications have high contrast to the surrounding tissues and high HU variations both inside the calcification area and at the edges. The contrast between calcification and background material is from −200 HU to −800 HU, and the HU standard deviation can be more than 200 HU. A calcification auto-detection scheme has been developed to locate the calcifications within CBBCT images. A 3D local thresholding process and a histogram thresholding process are first applied to the CBBCT images to select all voxels with relatively high HU value and HU variation with respect to the neighborhood voxels. To further reduce false positives, six features are extracted from each remaining connected voxel object. The features are fed into an artificial neural network (ANN) which is trained with known calcification features. The ANN output values are used as criteria to differentiate calcification objects from false positive objects. A preliminary study achieves sensitivity of 95% with average 10 false positives calcifications per case. FIG. 5 illustrates one example of CBBCT calcification auto-detection, in which image (a) indicates known calcifications and image (b) indicates eth results of the calcification algorithm. After the detection, measurements of the calcifications will be provided, including cluster size, number of calcifications in clusters and shape descriptors.

Breast ducts and blood vessels can be segmented. Segmenting algorithms are known in the art, e.g., for segmenting colons. A suitable algorithm is taught in D Chen, R Fahmi, A Farag, R L Falk, G W Dryden, "Accurate and fast 3D colon segmentation in CT colonography," Proc. of ISBI 2009; 490-493. Such segmentation can be used for active surveillance of duct carcinoma in situ (DICS) and abnormal vasculature relating to tumors.

Artifact correction will now be disclosed. A suitable method is taught in Ning R: Apparatus and Method for X-ray Scatter Reduction and Correction for Fan Beam and Cone Beam Volume CT. U.S. Pat. No. 6,618,466 issued on Sep. 9, 2003 and PCT/US03/04871.

Scattering is one of the major problems that are associated with CBBCT because the large-area flat-panel detector in a CBBCT system receives scattered x-rays as well as primary x-rays. At 49 kVp, the scatter-to-primary ratio can be as high as 0.5 for an average-sized breast. Scattering produces inaccurate CT numbers, reduces tissue contrast and causes cupping artifact in the reconstructed CBBCT images. Given the roughly symmetric geometry of a breast and the slowly varying nature of scattered radiation, the scattered radiation is estimated based on the breast shape in a projection image, and the projection image is corrected by subtracting the scattered radiation. As the shape and position and breast shadow are different across different projection images, such a correction is performed for all projections. The axial and longitude uniformity can be improved to 20 HU and 40 HU respectively.

Motion artifacts are associated with patient movement and breathing during the scan, appearing as blurs in the reconstruction images. Usually, the moment of motion can be identified by examining projection images. The data before or after this moment can be considered as motion-free data which can be used for reconstruction with half scan algorithms. A suitable algorithm is taught in Dong Yang, Ruola Ning, Yong Yu, David Conover and Xianghua Lu, "Implementation and evaluation of the half-scan scheme based on CBCT (cone-beam CT) system" Proc. SPIE 5368, 542 (2004). This method can efficiently remove motion artifacts.

Figure 6:
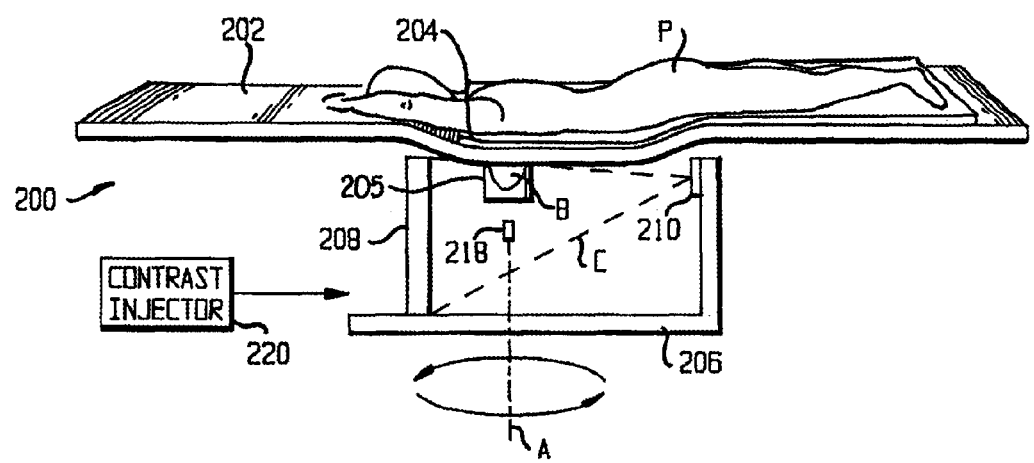
FIG. 6 is a schematic diagram showing an imaging system on which the preferred or another embodiment can be implemented.

A system on which the preferred or another embodiment can be implemented is set forth in U.S. Pat. No. 6,480,565, whose disclosure is hereby incorporated by reference in its entirety into the present disclosure. FIG. 2A of that patent, which is reproduced herein as FIG. 6, shows an exemplary device. In the scanner 200, the patient P rests on an ergonomically formed table 202 so that the breast B to be scanned descends through a hole 204 in the table 202 into a safety cover 205.

Below the table 202, a gantry 206 supports a detector 208 and an x-ray tube 210, one on either side of the safety cover 205. The gantry is turned by a motor 212 to be rotatable around an axis A passing through the safety cover 205, so that as the x-ray tube travels along an orbit O, the breast B remains in the path of a cone beam C emitted by the x-ray tube 210. The gantry is also movable by a motor 214 to go up and down along a vertical path V. Alternatively, the table 202 can be moved up and down along a vertical path V. The detector 208 can be moved toward and away from the axis A by a motor 216 to change the magnification factor if necessary.

In some embodiments, a piston 218 may be used to push the nipple toward the chest wall to reduce z-direction coverage by a couple of centimeters, although usually, the breast does not have to be re-shaped.

A contrast injector 220 can be provided for contrast enhanced tomographic imaging, angiogenesis studies and some other dynamic contrast studies. Various contrast injection media, such as iodine, are known in the art. It is not always necessary to inject a contrast medium into the patient.

Figure 7:
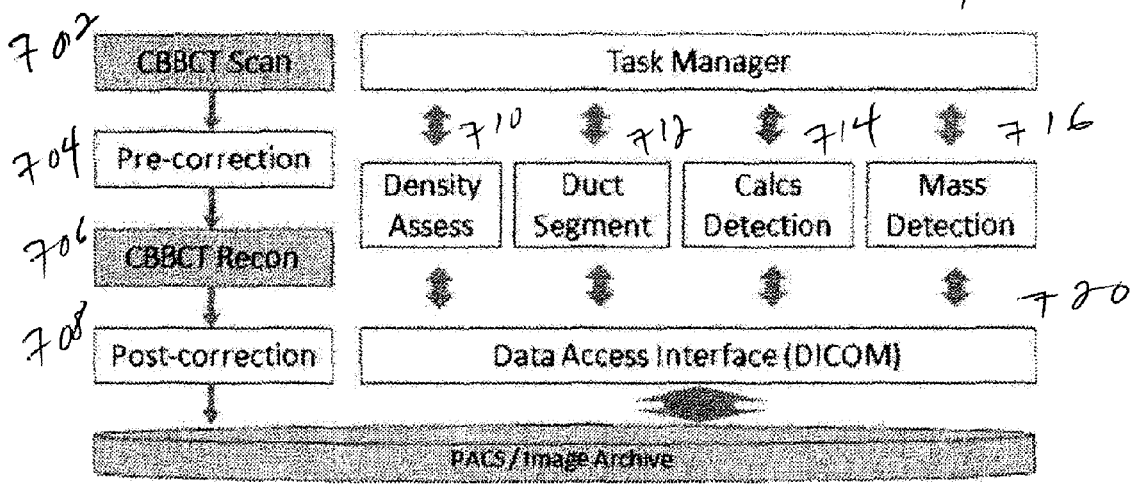
FIG. 7 is a block diagram of a software system for use in the preferred embodiment.

The CBBCT-CAD software/hardware includes the modules shown in FIG. 7:

Image Artifact Correction Modules: The image artifact correction modules are executed either before or after the CBBCT reconstruction. As shown, the modules include pre-correction 704 and post-correction 708. The pre-correction is performed on the projections acquired from the CBBCT scan. A suitable method is taught in Ning R: Apparatus and Method for X-ray Scatter Reduction and Correction for Fan Beam and Cone Beam Volume CT. U.S. Pat. No. 6,618,466 issued on Sep. 9, 2003 and PCT/US03/04871. The post-correction is performed on the isotropic 3D images from the CBBCT reconstruction.

Detection and Segmentation Modules: The four detection and segmentation modules are interconnected. Those modules are density assessment 710, duct segment detection 712, calcification detection 714, and mass detection 716. The density assessment algorithm has been described above. A suitable calcification detection algorithm is taught in Xiaohua Zhang, Ruola Ning and Jiangkun Liu, "Computer aided breast calcification auto-detection in cone beam breast CT," Proc. SPIE 2010; 7624: 76242M. A suitable mass detection algorithm is taught in Xiaohua Zhang, Ruola Ning and Dong Yang, "Three dimensional breast masses auto detection in cone beam breast CT," Proc. SPIE 2009; 7260: 726027. The users are able to choose one or multiple modules for better diagnostic assistance. Each of the modules is designed to run on both the CPU and the GPU to reduce the processing time. The output results of each module can be superimposed so that radiologists can combine different information to make an accurate decision.

The Task Manager 718 is the main interface of the CAD system between the users and the CAD modules. System connections, data send/receive configurations and task scheduling/queuing are defined through the task manager. The task manager organizes all applicable cases and dispatches the tasks to the detection and segmentation modules based on the specific requirements for each case. The task manager also plans all possible resources in the system and assigns the resource to the appropriate modules.

Data Access Interface 720: This is a DICOM interface to PACS/Image Archive system 722 for image data retrieve/store and the radiologists' feedback, annotation or report, for further processing. Multiple DICOM outputs, including DICOM printers, Structured Reporting, DICOM 6000 Overlay, Secondary Image Capture and RTSS are supported.

Figure 8:
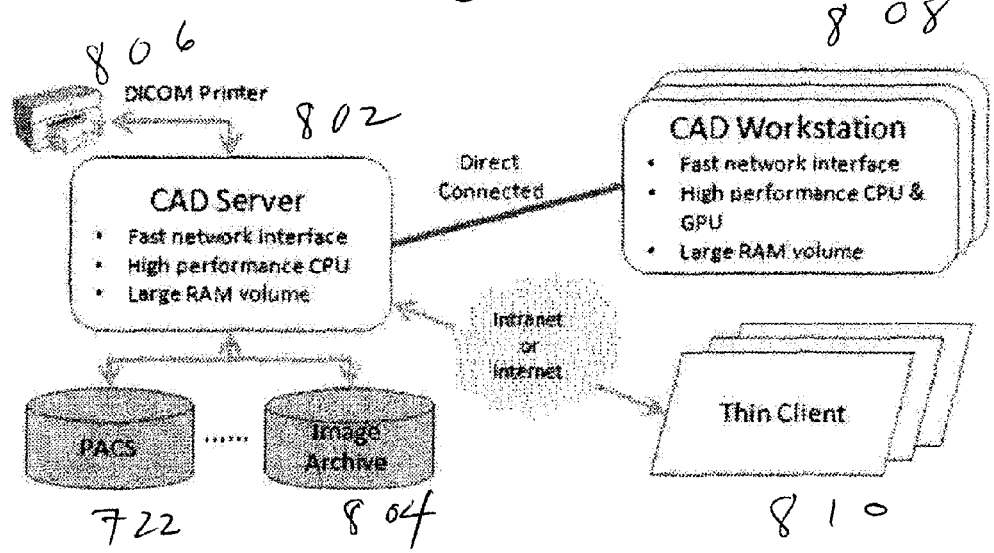
FIG. 8 is a block diagram of a hardware system for use in the preferred embodiment.

FIG. 8 shows the hardware structure of the CBBCT CAD system, based on the system of the above-cited '565 patent or any other suitable system. Three major hardware components will be included in the CAD system:

CAD Server 802: The CAD Server provides the interface for all clients and external PACS 722 or image archive systems 804, as well as DICOM printers 806. It is equipped with highly configured parts to provide fast and reliable services. The CAD server accepts the schedules from pre-configured tasks or the user inputs, read data from the PACS/Archive system, dispatches the computation tasks to the CAD workstations, receives the result from the workstations and writes the CAD reports back to the PACS/Archive system or prints the reports.

CAD Workstation 808: The major functional modules of the CAD system are running on the high performance workstation. It provides fast and reliable computation to satisfy the practical requirements. The workstation is attached to the server by hi-speed connection. Multiple workstations can be installed and connected in each system to perform the tasks parallelly to provide enough computation capability.

Thin Client 810: The thin client gives users easy access to the system. It can be browser-based application or stand-alone GUI application. It communicates with the CAD server within the intranet or over the internet to provide the services from anywhere with internet connection. The users setup the configurations and schedule tasks on the CAD server through the intuitive GUI provided by the thin client.

With the parallel processing capability of the hardware and software design, the total processing time of the CBBCT-CAD system is expected to be within 5 minutes.

While a preferred embodiment has been set forth in detail above, those skilled in the art who have reviewed the present disclosure will readily appreciate that other embodiments can be realized within the scope of the invention. For example, recitations of specific hardware and of numerical values are illustrative rather than limiting. In addition, the disclosed cone beam CT image-based CAD method and system can be used for other cone beam CT imaging applications, such as angiography imaging and lung imaging. Therefore, the present invention should be construed as limited only by the appended claims.

What is claimed is:

1. A method for imaging a breast of a patient, the method comprising:
    (a) taking three-dimensional (3D) cone-beam breast computed tomography (CBBCT) projection image data of the breast;
    (b) processing the projection image data taken in step (a) in a computing device for pre-reconstruction correction of the projection image data;
    (c) performing cone beam reconstruction of a matrix of 3D distribution of a linear attenuation coefficient of the breast in the computer device;
    (d) performing correction and processing after the reconstruction of the matrix of the breast in the computer device;
    (e) storing the corrected reconstruction matrix into an image archive device;
    (f) using a CPU-based computer device and a GPU-based computer device to perform the following plurality of tasks: detecting and characterizing mass, detecting calcifications, assessing breast density and detecting and characterizing duct system of the breast, based on the reconstructed 3D data;
    (g) outputting the composite breast information including locations, shapes and size(s) of mass(es) and calcifications, number of calcifications in volume of interest, breast density measurement and shapes of duct system of the breast; and
    (h) outputting the probability of malignancy of the breast based on the composite breast information determined in (g);
    wherein step (d) comprises: (a) detecting the skin of the breast and to remove the skin of the breast from the image data; (b) applying a stepwise fuzzy clustering algorithm in the computing device to the image data with the skin removed to adaptively cluster image voxels in the image data; (c) dividing the image data in the computing device into a plurality of categories; and (d) forming a three-dimensional image in the computing device from the image data divided into the plurality of categories.

2. The method of claim 1, wherein the plurality of categories comprise skin, fat, and glands.

3. The method of claim 1, wherein step (b) comprises: (i) separating the image data into air, fat, and tissues, using a histogram thresholding method; (ii) eroding the tissue between the air and the fat, using a morphological three-dimensional erosion operation with an erosion kernel; and (iii) stopping step (b)(ii) when the erosion kernel reaches a fat area in an inner portion of the breast.

4. The method of claim 1, wherein step (c) comprises: (A) separating the image data into air, fat, tissues, and a bias area; and (B) re-clustering the bias area to classify the bias area as air, fat, or tissues.

5. The method of claim 4, wherein the bias area arises from at least one of low-density glandular tissue and imaging artifacts.

6. The method of claim 1, wherein step (b) comprises: (i) recording a global ratio of a fat area to a total edge area along the edge of the breast; and (ii) stopping step (b) when the ratio reaches a predetermined value.

7. The method of claim 1, wherein the fuzzy clustering algorithm is a fuzzy c-means algorithm.

8. The method of claim 1, wherein (f), breast density is measured.

9. The method of claim 1, wherein (f) breast masses are detected.

10. The method of claim 1, wherein (f), breast calcifications are detected.

11. The method of claim 1, wherein (f) further comprising automatically or semi-automatically detecting and characterizing at least one of mass, calcifications, duct structure, vascular structure, and breast density.

12. A system for imaging a breast of a patient, the system comprising:
    an imaging apparatus for taking three-dimensional (3D) cone-beam breast computed tomography (CBBCT) projection image data of the breast;
    at least a computer device configured to process the projection image data taken in step (a) in a computing device for pre-reconstruction correction of the projection image data;
    to perform cone beam reconstruction of a matrix of 3D distribution of linear attenuation coefficient of the breast;
    to perform correction and processing after the reconstruction of the matrix of the breast in the computer device;
    a massive data storage/archive device to store the corrected reconstruction matrix into image archive device;
    at least a computer device comprising a CPU-based computer device and a GPU-based computer device to perform following plurality of tasks: detecting and characterizing mass, detecting calcifications, assessing breast density and detecting and characterizing duct system of the breast, based on the reconstructed 3D data;
    outputting the composite breast information including locations, shapes and size(s) of mass(es) and calcifications, number of calcifications in volume of interest, breast density measurement and shapes of duct system of the breast;
    outputting the probability of malignancy of the breast based on the composite breast information determined in previous step;
    said system further comprising: a processor, in communication with the imaging apparatus, configured for processing the image data taken by the imaging apparatus to detect the skin of the breast and to remove the skin of the breast from the image data; applying a stepwise fuzzy clustering algorithm to the image data with the skin removed to adaptively cluster image voxels in the image data;
    dividing the image data into a plurality of categories; and forming a three-dimensional image from the image data divided into the three categories; and an output, in communication with the processor, for outputting the image.

13. The system of claim 12, wherein the plurality of categories comprise skin, fat, and glands.

14. The system of claim 13, wherein the processor is configured for: (i) separating the image data into air, fat, and tissues, using a histogram thresholding method; (ii) eroding the tissue between the air and the fat, using a morphological three-dimensional erosion operation with an erosion kernel; and (iii) stopping step (ii) when the erosion kernel reaches a fat area in an inner portion of the breast.

15. The system of claim 14, wherein the processor is configured such that step (i) comprises: (A) separating the image data into air, fat, tissues, and a bias area; and (B) re-clustering the bias area to classify the bias area as air, fat, or tissues.

16. The system of claim 12, wherein the processor is configured for a situation in which the bias area arises from at least one of low-density glandular tissue and imaging artifacts.

17. The system of claim 12, wherein the processor is configured for: (i) recording a global ratio of a fat area to a total edge area along the edge of the breast; and (ii) stopping step (b) when the ratio reaches a predetermined value.

18. The system of claim 12, wherein the processor is configured such that the fuzzy clustering algorithm is a fuzzy c-means algorithm.

19. The system of claim 12, wherein the processor is configured to measure breast density.

20. The system of claim 12, wherein the processor is configured to detect breast masses.

21. The system of claim 12, wherein the processor is configured to detect breast calcifications.

22. The system of claim 12, wherein the processor is configured for automatically or semi-automatically detecting and characterizing at least one of mass, calcifications, duct structure, vascular structure, and breast density.

* * * * *